(12) United States Patent
He

(10) Patent No.: US 9,636,084 B2
(45) Date of Patent: May 2, 2017

(54) APPARATUS AND METHOD FOR MEASURING SUBCUTANEOUS FAT THICKNESS USING ULTRASOUND

(71) Applicant: Lina He, Burke, VA (US)

(72) Inventor: Lina He, Burke, VA (US)

(73) Assignee: Lina He, Burke, VA (US)

( * ) Notice: Subject to any disclaimer, the term of this patent is extended or adjusted under 35 U.S.C. 154(b) by 322 days.

(21) Appl. No.: 14/588,921

(22) Filed: Jan. 3, 2015

(65) Prior Publication Data
US 2016/0192899 A1     Jul. 7, 2016

(51) Int. Cl.
*A61B 8/14*     (2006.01)
*A61B 8/08*     (2006.01)
*A61B 8/00*     (2006.01)

(52) U.S. Cl.
CPC .......... *A61B 8/0858* (2013.01); *A61B 8/5223* (2013.01); *A61B 8/4483* (2013.01); *A61B 8/467* (2013.01)

(58) Field of Classification Search
CPC ..... A61B 8/0858; A61B 8/4483; A61B 8/467; A61B 8/5223
See application file for complete search history.

(56) References Cited

U.S. PATENT DOCUMENTS

| | | |
|---|---|---|
| 5,941,825 A | 8/1999 | Lang |
| 6,282,962 B1 | 9/2001 | Koch |
| 2005/0197575 A1 | 9/2005 | Kondoh |
| 2006/0184024 A1 | 8/2006 | Da Silva |
| 2013/0123629 A1 | 5/2013 | Rosenberg |

OTHER PUBLICATIONS

Body Metrix User's Guide, [online], http://www.intelametrix.com, 2011.
Instruction for using Lean-Meater [online], http://www.rencocorp.com, 2013.

*Primary Examiner* — Mark Remaly

(57) ABSTRACT

An apparatus and a method for measuring subcutaneous fat thickness using amplitude mode (A-mode) ultrasound technology are proposed. An echo peak generated at a fat-muscle boundary is distinguished from other echo peaks generated at muscle-bone boundaries or at muscle-muscle boundaries. The discrimination of echo peaks is based on echo time delay change when applying variable pressure to an ultrasound transducer. Statistical information of echo peak time delay change is estimated and is used for determine an echo peak generated at the fat-muscle boundary.

6 Claims, 5 Drawing Sheets

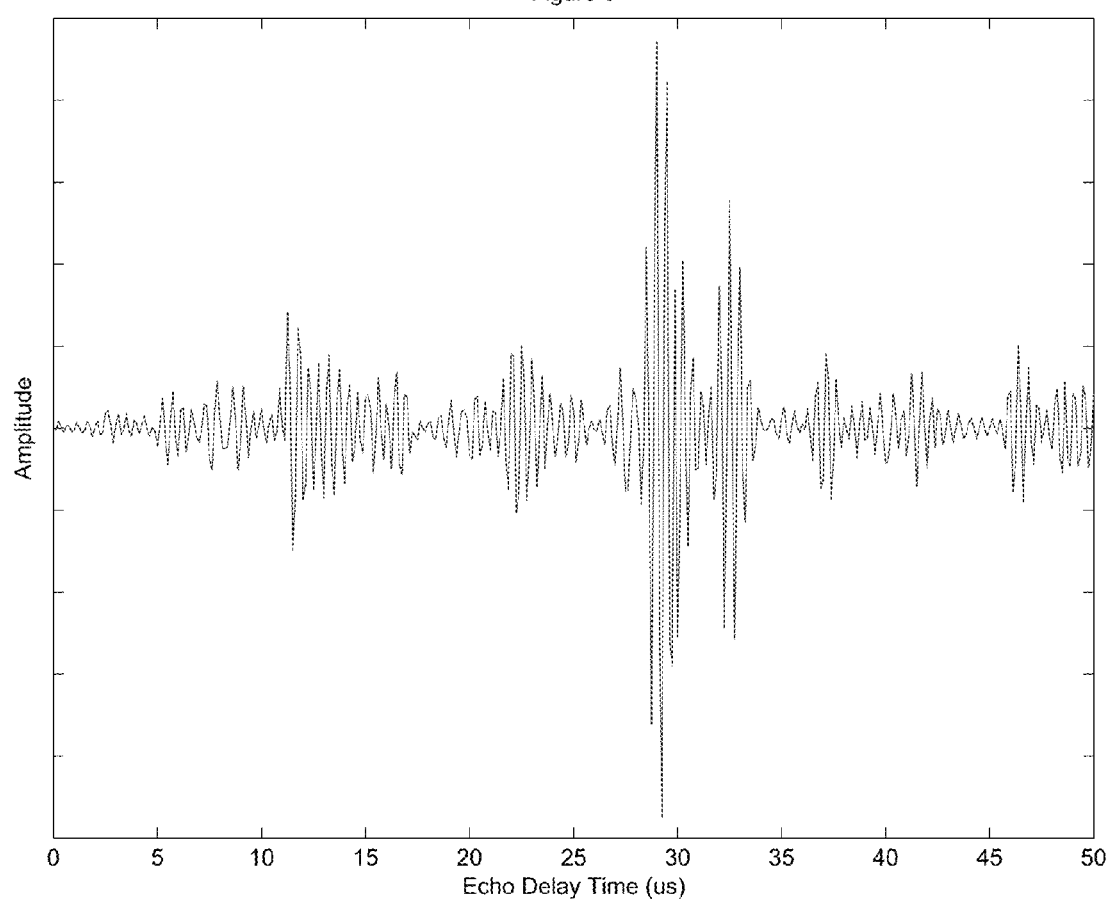

ial can be calculated using a simple formula. However, the human body is more complicated and has multiple layers underneath the skin. The thickness of each layer is not uniform. An industrial thickness gauge that is used for measuring metal thickness can not be used to measure subcutaneous fat thickness of the human body.

APPARATUS AND METHOD FOR MEASURING SUBCUTANEOUS FAT THICKNESS USING ULTRASOUND

BACKGROUND

Field of the Invention:

Embodiments described herein related generally to an apparatus and a method for measuring subcutaneous fat thickness using amplitude mode (A-mode) ultrasound technology.

Description of the Related Art: There are several ways to measure subcutaneous (i.e., under the skin) fat thickness. One method is using a skin fold caliper. By using this method, skin and fat at a measuring spot is pinched and folded. The total thickness is measured using the caliper. The measured thickness depends on how tight the skin and fat layers are pinched. Another problem of using this method is that one can not fold skin and fat layers at certain body locations.

The second method of measuring subcutaneous fat thickness is using ultrasound technology. Studies have been conducted using hospital ultrasound machines to measure skin fat thickness. The fat thickness is obtained by measuring distances on a two-dimensional ultrasound image which is formed using a brightness mode (B-mode) scan. A disadvantage of this method is that the ultrasound machines used in hospitals are expensive.

Another method of measuring subcutaneous fat thickness is using A-Mode ultrasound technology. The basic idea is similar to that of an industrial thickness gauge. The thickness gauge first sends an ultrasound pulse and then receives an echo signal. Based on the known velocity of sound in a measured material and the measured echo time delay (often called "time-of-flight"), the thickness of the measured material can be calculated using a simple formula. However, the human body is more complicated and has multiple layers underneath the skin. The thickness of each layer is not uniform. An industrial thickness gauge that is used for measuring metal thickness can not be used to measure subcutaneous fat thickness of the human body.

An ultrasound device (BodyMetrix™) is available on the market for measuring skin fat thickness. BodyMetrix uses A-mode ultrasound to measure subcutaneous fat thickness. After sending out one ultrasound pulse, the device receives an echo having multiple peaks caused by multiple layers underneath the skin. BodyMetrix assumes that the first strong peak is an echo generated from a fat-muscle boundary. However, the inventor of the current application noticed that this assumption is not always true. Sometimes, BodyMetrix picks an echo peak that is not generated at the fat-muscle boundary. Therefore, the calculated subcutaneous fat thickness is incorrect.

SUMMARY

The objective of the invention is to provide a method and an apparatus for accurately measuring subcutaneous fat thickness using the amplitude mode (A-mode) ultrasound technology. For one ultrasound pulse, multiple echo peaks are received because of the complicated structure underneath the skin. In order to accurately calculate the fat layer thickness, it is necessary to determine which echo peak among the multiple peaks is generated from the fat-muscle boundary.

In one embodiment, an ultrasound transducer is put in contact with a testing spot on the skin surface. A variable pressure is applied to the ultrasound transducer. An echo peak generated at a fat-muscle boundary is distinguished from other echo peaks generated at muscle-bone or muscle-muscle boundaries based on different time delay changes under the variable pressure.

BRIEF DESCRIPTION OF THE DRAWINGS

The present method and apparatus will be understood and appreciated from the following detailed description, taken in conjunction with the drawings in which:

FIG. 3 is a recorded ultrasound echo waveform from a testing spot on a human leg by sending an ultrasound pulse.

DETAILED DESCRIPTION

Figure 1:
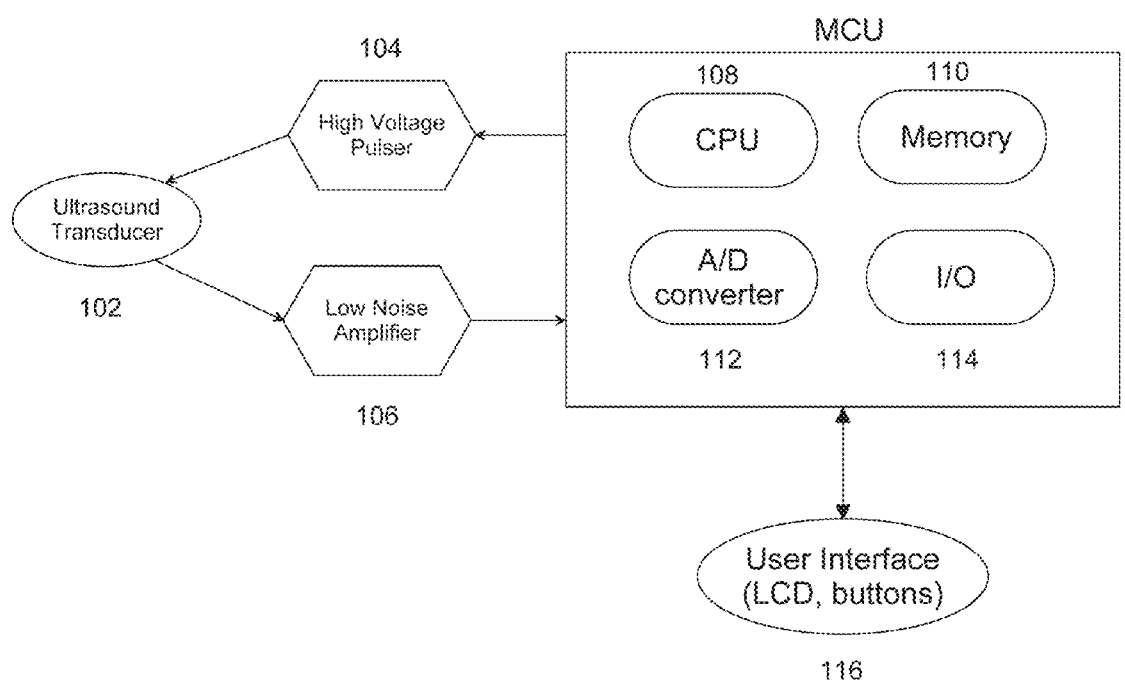
FIG. 1 is a block diagram showing an apparatus of the current invention for measuring subcutaneous fat thickness.

FIG. 1 is a block diagram of a subcutaneous fat thickness measuring apparatus. The apparatus includes an ultrasound transducer 102, a high-voltage (HV) pulser 104 and a low noise amplifier 106. The transducer 102 can be a single element transducer or a dual-element transducer. The HV pulser 104 and the amplifier 106 are controlled under a microcontroller unit (MCU). The MCU has a central processing unit (CPU) 108, memory 110 and Input/Output (I/O) interface 114. The received echo signals are amplified and converted to digital signals using an Analog-to-Digital (A/D) converter 112. The MCU also communicates with user interface elements 116 to display measured results.

Figure 2:
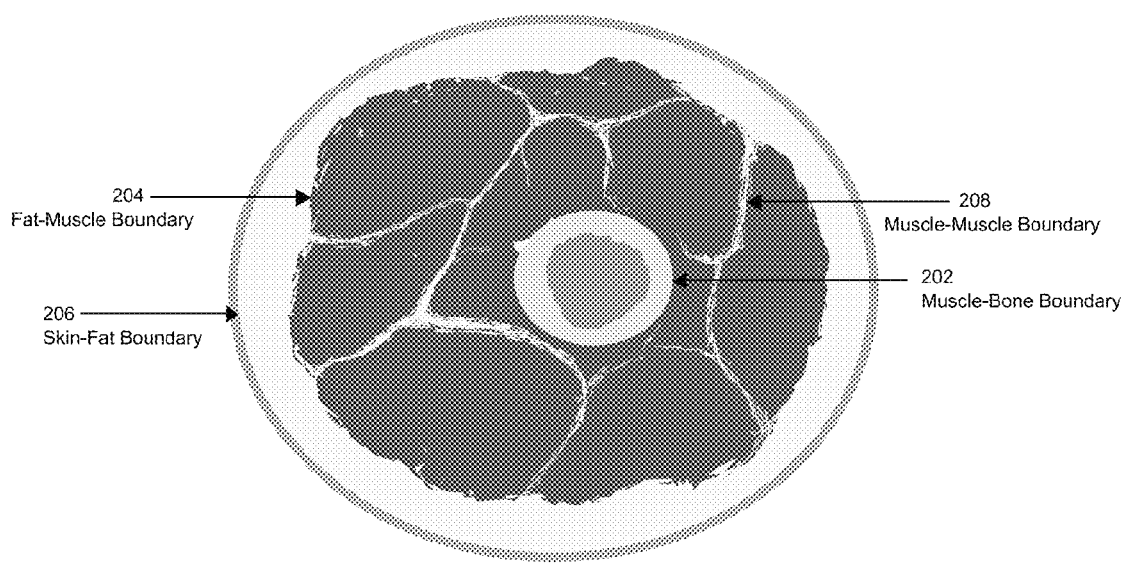
FIG. 2 is an illustration of the cross-section of a human leg which has a multi-layer structure.

FIG. 2 is an illustration of the cross-section of a human leg. The basic structure of the cross-section may include a skin layer, fat layers, muscle layers and bones. The thickness of fat layers is not uniform and changes from one spot to another. The muscle is not a single layer but composed of many fascicles. When applying a certain pressure on the surface of the skin, the thickness of muscle changes largely because muscle fascicles are moveable and escape to the sides of the pressed point.

FIG. 3 shows a recorded echo signal by sending an ultrasound pulse to a spot on a human leg. The horizontal axis represents time and the vertical axis represents signal amplitude. It can be seen that for one driving pulse, the received echo signal has multiple energy peaks. It is not easy to determine which energy peak is generated from a fat-muscle boundary. Prior art method assumes the first strong peak is an echo from the fat-muscle boundary. The inventor of this application noticed that this assumption is not always true. If a wrong energy peak is selected as the echo from a fat-muscle boundary, the calculated fat thickness is incorrect.

Through extensive experiments, the inventor discovered that when applying variable pressure to the ultrasound transducer, the energy peak positions generated from fat-muscle boundaries shifted relatively less along the time axis with pressure changes. On the other hand, the energy peaks positions generated from muscle-bone boundaries or from muscle-muscle boundaries shifted more. This observation shows that fat thickness can not be compressed as much under pressure, but muscle thickness can be compressed due to its structure. Muscle is composed of fascicles. These fascicles are moveable and move to the sides of the transducer under a certain pressure. Since echo peaks from different boundaries shift differently under variable pressure, it is possible to distinguish echo peaks generated at a fat-muscle boundary from echo peaks generated at muscle-bone or muscle-muscle boundaries.

Figure 4A:
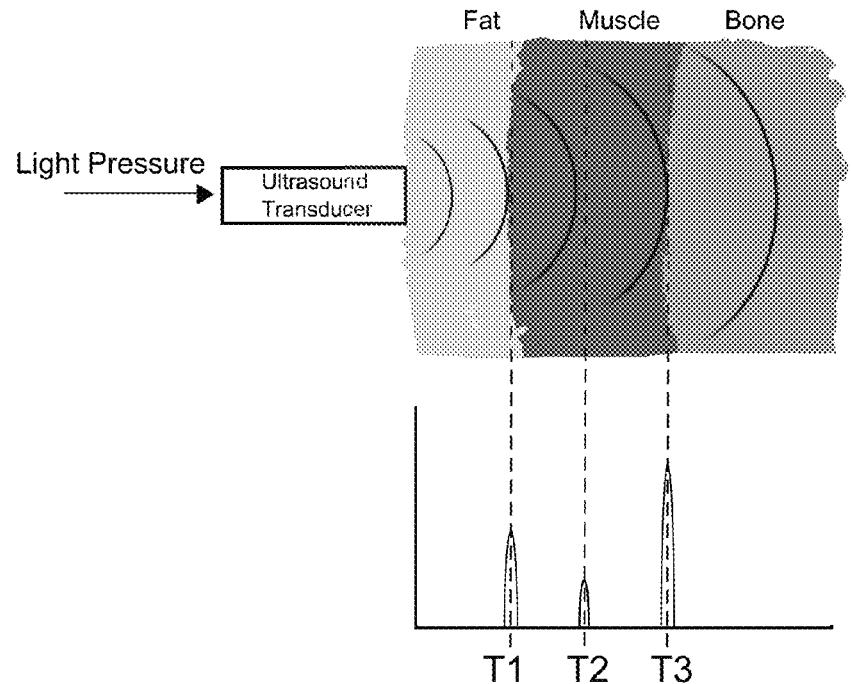
FIG. 4A and 4B illustrates time delay changes of echo peaks when applying variable pressures.

FIG. 4A illustrates echo peaks obtained when an ultrasound transducer is under a light pressure. $T_1$ is a time delay of an echo peak generated at a fat-muscle boundary. Similarly, $T_2$ and $T_3$ are time delays of echo peaks generated at a muscle-muscle boundary and at a muscle-bone boundary, respectively.

Figure 4B:
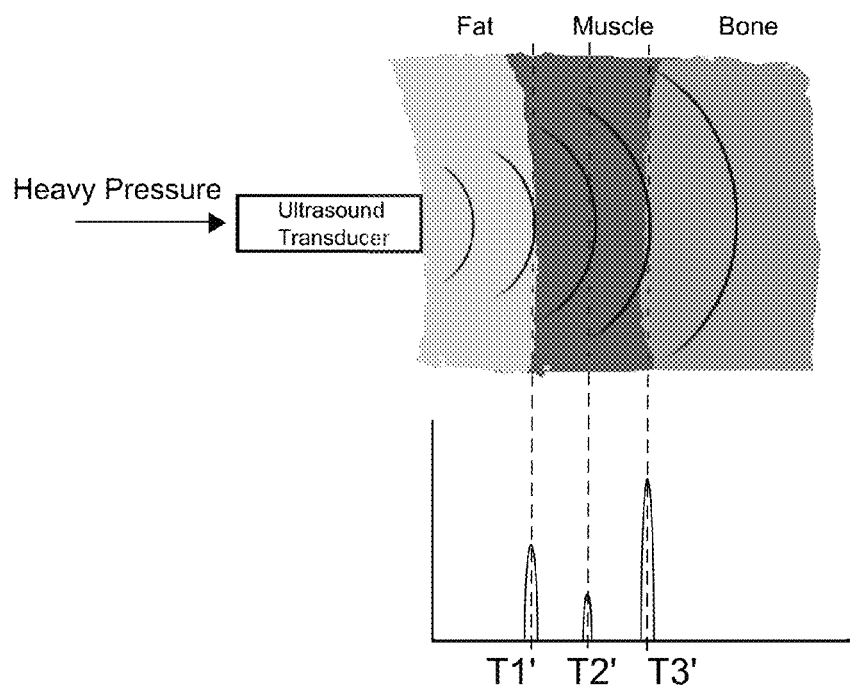

FIG. 4B illustrates echo peaks obtained when the ultrasound transducer is under a heavier pressure. The fat layer can not be compressed as much. Therefore, the time delay change, $\Delta T_{fat}=(T_1-T_1')$, is relatively small under different pressures. While the time delay change of echo peaks at a muscle-bone boundary, $\Delta T_{bone}=(T_3-T_3')$, and at a muscle-muscle boundary, $\Delta T_{muscle}=(T_2-T_2')$, are larger compared to $\Delta T_{fat}$. By comparing echo time delay changes under variable pressures, it is possible to distinguish echo peaks generated at fat-muscle boundaries from these echoes generated at muscle-bone (or muscle-muscle) boundaries. When applying variable pressures to an ultrasound transducer, an echo peak with a smaller time delay change is likely generated at a fat-muscle boundary. In other words, a relatively stable echo peak under variable pressure is selected for calculating the subcutaneous fat thickness.

Figure 5:
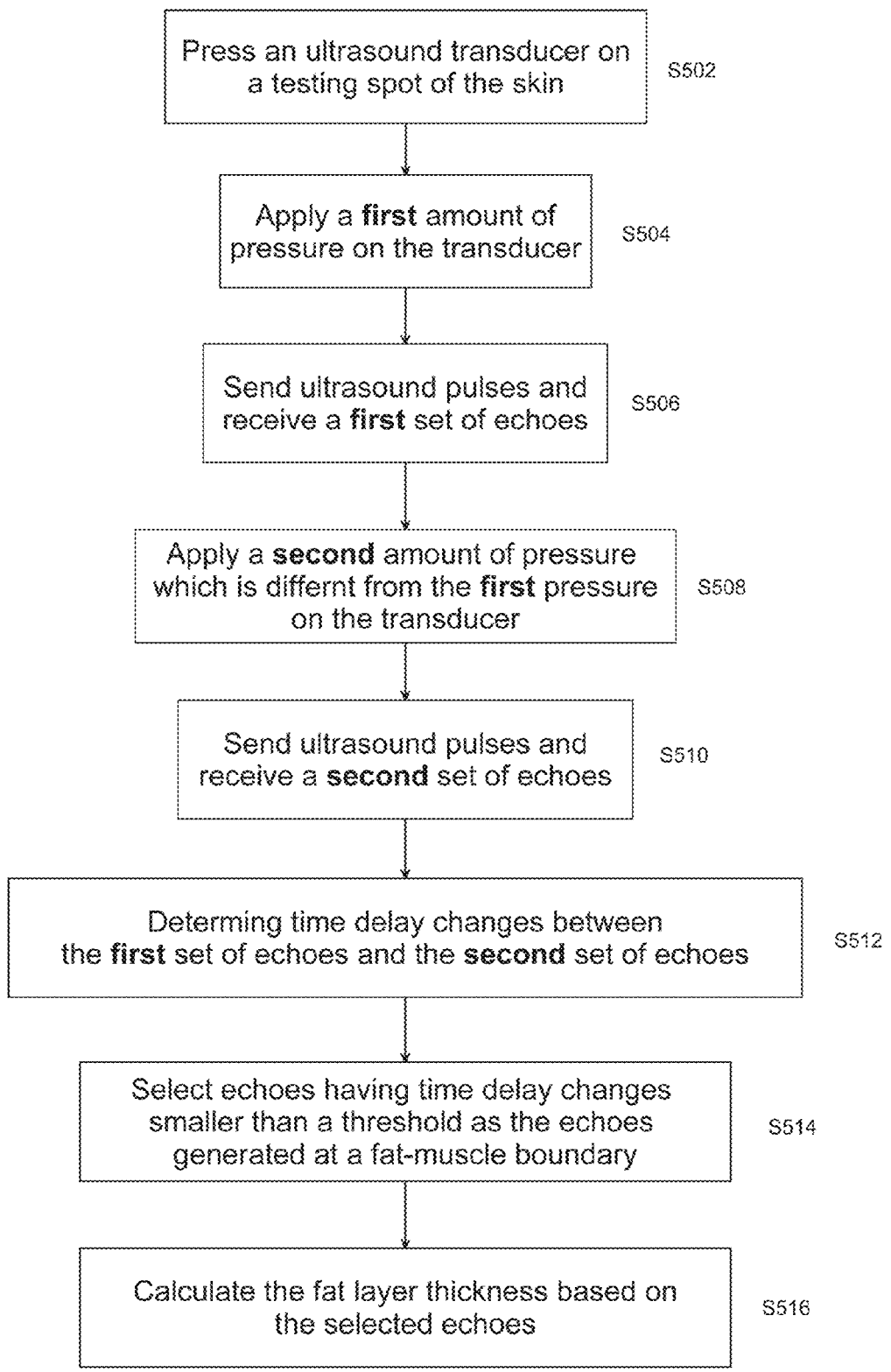
FIG. 5 is a flowchart showing a method of the current invention for measuring subcutaneous fat thickness.

FIG. 5 is a flow diagram of a method of measuring subcutaneous fat thickness. The method of testing fat thickness includes the following steps:
Put an ultrasound transducer on a testing spot of the skin surface;
Apply a light pressure to the transducer;
Send an ultrasound pulse and receive a first set of echoes;
Apply a heavier pressure to the transducer;
Send an ultrasound pulse and receiving a second set of echoes;
Determine time delay changes between two sets of echoes received under different pressures;
Select an echo peak with a smaller time delay change under different pressures as the echo peak generated at the fat-muscle boundary for calculating fat thickness.

In practice, just a single pass pressure change is not reliable enough to distinguish an echo peak generated at fat-muscle layer from other echo peaks. The test steps S504-S510 should be repeated multiple times. In other words, the ultrasound transducer is repeatedly pressed and released with varying amount of pressure. Throughout the process, the ultrasound transducer keeps sending ultrasound pulses and receiving echoes. Statistic measurements including mean value and/or deviation are evaluated from the received echo peak positions.

In a specific implementation, it is assumed that the maximum subcutaneous fat thickness is 40 millimeter. A known velocity of sound in fat is about 1450 m/s. The maximum echo delay time for a 40 mm fat layer is about 55 microseconds. The total echo delay time range is divided into time slices, for example, in 0.5 μs increments. Echo peak occurrence frequency in each time slice is counted. If the echo peak occurrence frequency in a time slice is larger than a threshold, it assumes that a stable layer exists under variable pressure. This stable layer could be a fat layer and its thickness is calculated based on the corresponding echo peak position.

What is claimed is:
1. An apparatus for measuring subcutaneous fat thickness by ultrasound, comprising:
a central processing unit (CPU) and associated memory;
a transducer for sending ultrasound pulses and receiving ultrasound echoes;
computer program code stored in the memory and executed by the CPU;
the apparatus controlled by the CPU performs functions comprising:
applying a first amount of pressure to the transducer in contact with a skin spot;
sending a first one or more ultrasound pulses from the transducer while applying said first amount pressure on said skin spot;
receiving a first set of echoes;
deriving a first plurality of echo peak positions from the first set of echoes;
applying a second amount of pressure to the transducer in contact with said skin spot, wherein said second amount of pressure is different from said first amount of pressure;
sending a second one or more ultrasound pulses from the transducer while applying said second amount pressure on said skin spot;
receiving a second set of echoes;
deriving a second plurality of echo peak positions from the second set of echoes;
distinguishing echoes generated at a fat-muscle boundary from echoes generated at muscle-bone boundaries based on time delay changes between said first plurality of echo peak positions and said second plurality of echo peak positions;
determining at least one echo as being generated at the fat-muscle boundary if said at least one echo has a time delay change being smaller than a first threshold;
calculating the subcutaneous fat thickness based on the determined at least one echo as being generated at the fat-muscle boundary.
2. The apparatus of claim 1, the functions further comprising:
repeating N times of applying the first amount of pressure and applying the second amount of pressure to the transducer, where N>1;
sending one or more ultrasound pulses and receiving echoes for each of the repeated N times;
calculating statistic values of the time delay changes based on echoes received from the repeated N times;
determining the at least one echo as being generated at the fat-muscle boundary based on the statistic values of the time delay changes.
3. The apparatus of claim 2, the functions further comprising:
dividing a pre-determined echo time delay range into a plurality of time slices;
calculating an echo peak occurrence frequency for each time slice of the plurality of time slices;
selecting a time slice having an echo peak occurrence frequency larger than a second threshold as a peak position of the at least one echo generated at the fat-muscle boundary;
calculating the subcutaneous fat thickness based on the selected time slice.
4. A method for measuring subcutaneous fat thickness by ultrasound, comprising:
applying a first amount of pressure to a transducer in contact with a skin spot;

sending a first one or more ultrasound pulses from the transducer while applying said first amount of pressure on said skin spot;

receiving a first set of echoes;

deriving a first plurality of echo peak positions from the first set of echoes;

applying a second amount of pressure to the transducer in contact with said skin spot, wherein said second amount of pressure is different from said first amount of pressure;

sending a second one or more ultrasound pulses from the transducer while applying said second amount pressure on said skin spot;

receiving a second set of echoes;

deriving a second plurality of echo peak positions from the second set of echoes;

distinguishing echoes generated at a fat-muscle boundary from echoes generated at muscle-bone boundaries based on time delay changes between said first plurality of echo peak positions and said second plurality of echo peak positions;

determining at least one echo as being generated at the fat-muscle boundary if said at least one echo has a time delay change being smaller than a first threshold;

calculating the subcutaneous fat thickness based on the determined at least one echo as being generated at the fat-muscle boundary.

5. The method of claim 4, further comprising:

repeating N times of applying the first amount of pressure and applying the second amount of pressure to the transducer, where N>1;

sending one or more ultrasound pulses and receiving echoes for each of the repeated N times;

calculating statistic values of the time delay changes based on echoes received from the repeated N times;

determining the at least one echo as being generated at the fat-muscle boundary based on the statistic values of the time delay changes.

6. The method of claim 5, further comprising:

dividing a pre-determined echo time delay range into a plurality of time slices;

calculating an echo peak occurrence frequency for each time slice of the plurality of time slices;

selecting a time slice having the peak occurrence frequency larger than a second threshold as a peak position of the at least one echo generated at the fat-muscle boundary;

calculating the subcutaneous fat thickness based on the selected time slice.

* * * * *